(12) United States Patent
Amaravadi

(10) Patent No.: US 10,365,260 B2
(45) Date of Patent: Jul. 30, 2019

(54) IMAGE BASED SURVEILLANCE SYSTEM

(71) Applicant: Honeywell International Inc., Morristown, NJ (US)

(72) Inventor: Vijayapavan Amaravadi, Hyderabad (IN)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 893 days.

(21) Appl. No.: 14/584,027

(22) Filed: Dec. 29, 2014

(65) Prior Publication Data

US 2016/0187310 A1  Jun. 30, 2016

(51) Int. Cl.
| | |
|---|---|
| *G01N 31/00* | (2006.01) |
| *G01N 33/00* | (2006.01) |
| *G08B 21/14* | (2006.01) |
| *G08B 25/14* | (2006.01) |

(52) U.S. Cl.
CPC ......... *G01N 33/0062* (2013.01); *G08B 21/14* (2013.01); *G08B 25/14* (2013.01)

(58) Field of Classification Search
CPC ..... G01N 33/0062; G08B 21/14; G08B 25/14
See application file for complete search history.

(56) References Cited

U.S. PATENT DOCUMENTS

| | | | | |
|---|---|---|---|---|
| 2,883,255 A | * | 4/1959 | Anderson ................ | B41J 11/36 340/518 |
| 3,415,108 A | * | 12/1968 | Hubner .................. | G01N 27/16 73/23.2 |
| 4,795,253 A | * | 1/1989 | Sandridge ................ | G01J 3/02 250/338.5 |
| 5,025,653 A | * | 6/1991 | Schuldt ............. | G01N 33/0032 73/23.2 |
| 6,252,510 B1 | * | 6/2001 | Dungan ............. | G01N 33/0075 340/539.1 |
| 6,670,887 B2 | * | 12/2003 | Dungan ............. | G01N 33/0075 340/539.26 |

(Continued)

FOREIGN PATENT DOCUMENTS

| | | |
|---|---|---|
| CN | 107438766 A | 12/2017 |
| EP | 3241199 | 11/2017 |
| WO | 2016109197 A1 | 7/2016 |

OTHER PUBLICATIONS

International Application No. PCT/US2015/065991, International Preliminary Report on Patentability, dated Jul. 13, 2017, 9 pages.

(Continued)

*Primary Examiner* — Toan M Le
*Assistant Examiner* — Xuiqin Sun
(74) *Attorney, Agent, or Firm* — Wick Phillips Gould & Martin, LLP

(57) ABSTRACT

A method incorporating the steps of a display of a gas detection system depicting a map of a predetermined geographic area and a plurality of portable gas detectors on the map via a respective gas detector icon, a programmed processor of the gas detection system identifying a number of gas detectors of the plurality of portable gas detectors within a predetermined portion of the area depicted on the display, the number exceeding a threshold value and a programmed processor of the gas detection system replacing the icons of the identified gas detectors within the portion with a group icon.

20 Claims, 3 Drawing Sheets

(56) References Cited

U.S. PATENT DOCUMENTS

| | | | |
|---|---|---|---|
| 6,794,991 B2* | 9/2004 | Dungan | G01N 33/0073 340/539.19 |
| 2001/0040509 A1* | 11/2001 | Dungan | G01N 33/0075 340/632 |
| 2002/0070869 A1* | 6/2002 | Dungan | G01N 33/0073 340/632 |
| 2004/0056771 A1* | 3/2004 | Dungan | G01N 33/0075 340/632 |
| 2008/0097731 A1 | 4/2008 | Lanes et al. | |
| 2008/0133653 A1 | 6/2008 | Fok | |
| 2014/0226951 A1 | 8/2014 | Wu et al. | |
| 2015/0106033 A1* | 4/2015 | Beerndt | G01N 33/0065 702/24 |

OTHER PUBLICATIONS

Europe Patent Application No. 15820959.3, Communication Pursuant to Rules 161(1) and 162 EPC, dated Aug. 4, 2017, 2 pages.
International Application No. PCT/US2015/065991, International Search Report, dated Mar. 9, 2016, 4 pages.
International Application No. PCT/US2015/065991, Written Opinion of the International Searching Authority, dated Mar. 9, 2016, 7 pages.

\* cited by examiner

IMAGE BASED SURVEILLANCE SYSTEM

FIELD

This application relates to safety systems and more particular to hazardous gas detection systems.

BACKGROUND

Systems are known to protect people and assets from hazardous and combustible gas leaks within areas under surveillance. Such systems are typically based upon the use of a number of gas sensors distributed throughout the area under surveillance.

For example, carbon monoxide detectors may be located near sleeping areas in residences. Similarly, smoke or carbon monoxide detectors may be placed in a kitchen or near a home's heating system.

In an industrial setting involving the use of toxic gases (e.g., hydrogen sulfide, hydrogen dioxide, etc.), one or more gas detectors may be placed near a source and/or a point of consumption of the toxic gas. Gas and/or smoke detectors may also be located throughout the area for the additional protection of people working in the area. Individuals may also wear portable gas detectors which will help in gas detection while moving around the area.

Gas detectors (fixed and portable) within an area are often coupled to a central monitoring panel. In this case, each gas detector may periodically measure a gas level proximate the device and report its readings to the central monitoring panel. The central monitoring system may receive a gas reading from each gas detector and sound a general (or local) alarm if the detected gas exceeds some threshold level. In addition to gas detection, the devices can also communicate about man down, panic situations and compliance dues. Device has an accelerometer to communicate about Man Down situation if the device user does not move for a specified time. Device user him/herself can trigger a Panic situation by pressing a button on the device as needed.

A display may be used in conjunction with the central monitoring panel. The display may show a map of the area under surveillance and the location of any activated sensors within the area.

While such systems work well, they are often difficult to use. For example, some areas may have hundreds of gas detectors. In such cases, it is difficult for a central monitoring system to reliably receive a reading from each detector and act upon those readings in an expeditious manner. Accordingly, a need exists for better methods of receiving readings from gas detectors and displaying those readings on a central monitoring panel.

DETAILED DESCRIPTION

Figure 1:
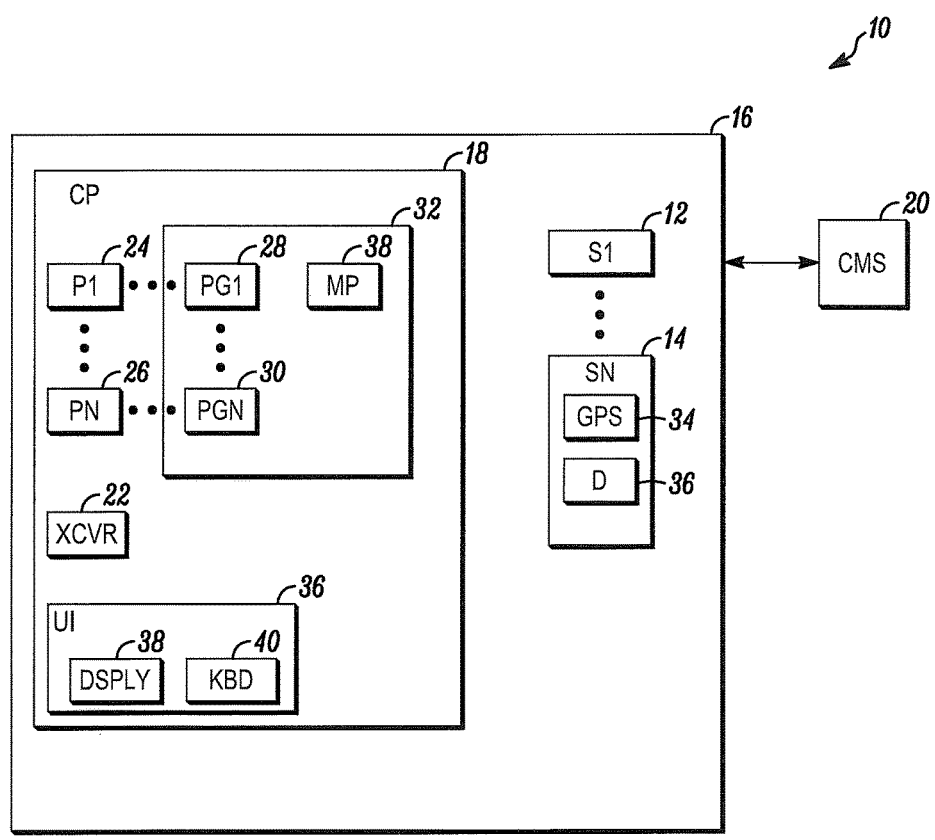
FIG. 1 illustrates a block diagram of a safety system in accordance herewith.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

FIG. 1 is a simplified block diagram of a safety system (e.g., a gas monitoring system) 10 shown generally in accordance with an illustrated embodiment. Included within the system is a number of wireless portable detectors (e.g., gas detectors) 12, 14 that detect threats to people and assets within the geographic area 16 under surveillance.

A control panel 18 may monitor each of the detectors for gas levels above a threshold value and for also panic and man-down situations. Upon detecting a gas sensor crossing the threshold value, the control panel may compose and send an alarm message to a central monitoring station 20. The alarm message may include an identifier of the alarm system (e.g., address, account number, etc.), an identifier of the type of alarm and a location of the alarm within the secured area. The central monitoring station may respond by summoning help (e.g., paramedics or other emergency responders, fire department, etc.).

While the control panel is shown within the area under surveillance, it may also be located remotely. Similarly, while the central monitoring station is shown to be remotely located, the central monitoring station may also be located within the area under surveillance.

Included within the control panel and each of the wireless portable gas detectors is a radio frequency transceiver 22. The control panel and each of the wireless detectors may exchange messages under any of a number of different formats (e.g., TDMA, FDMA, etc.).

Also included within the control panel and each of the portable detectors is one or more processor apparatus (processors) 24, 26. Each of the processors may operate under control of one or more computer programs 28, 30 loaded from a non-transitory computer readable medium (memory) 32. As used herein, reference to a step performed by a computer program is also reference to the processor that executed that step.

At least some or all of the portable detectors may also include a position detection device 34. The position detection device may be a GPS device or a triangulating processor that determines the detector's position by reading three or more signal strength values from a set of radio frequency beacons distributed around a periphery of the area under surveillance. A tracking processor within the detector may periodically determine the detector's geographic location and report that location to the control panel.

Similarly, a gas reading processor within each detector may retrieve a gas reading from a respective sensor 36 and compare that reading with a threshold value saved within a memory of the detector. If the reading exceeds the threshold value, then the gas reading processor or a separate reporting processor may send an alarm or high gas reading message to the control panel. The high gas reading message may include an identifier of the detector, the gas reading retrieved from the sensor and an indicator that the gas reading has exceeded the threshold value. The message may also include a recently determined geographic location of the detector at the time of the high gas reading.

Alternatively, the gas reading processor may simply retrieve a gas reading and transmit the gas reading and location of gas reading to the control panel. In this case, the threshold value for each detector may be saved within the memory of the control panel. In response, the alarm is determined within the control panel by comparing the reading with the threshold value.

Included within memory of the control panel may be a map of the area under surveillance. The map may be embodied as a set of geographic features of the area under surveillance (e.g., doors, walls, parking lots, etc.) and a respective geographic coordinate of each feature saved within a file 38.

The safety system may be monitored by a security guard or control room operator via a user interface 36. The user interface may include a display 38 and a keyboard 40.

The security guard or control room operator may monitor the status of the area under surveillance by activating a display processor via the keyboard. The display processor may retrieve the map from the map file and present the map of the display. A location processor may determine a geographic location of each of the portable detectors with respect to the map coordinates and display a respective icon on the map at a corresponding location of the detector.

A status processor may then determine a status of each of the gas detectors and color the respective icons shown in the map. For example, a red icon may indicate an alarmed device or sensor (i.e., the gas read reading exceeds the threshold or device indicates a man down state or panic alarm). An amber icon may indicate that a device calibration is due, that the gas reading does not represent a valid value or that the control panel cannot contact the detector. A green icon indicates that the control panel is in contact with the detector and that the gas reading is in a normal range and does not exceed the threshold value.

In general, the display and status processors may be control room applications whose functionality is accomplished via a number of different safety system programs (e.g., LocaXion Manager (LM) of ConneXt Safety Solutions Pro). The processors allow a guard or other user to perform hazardous gas detection and location identification of field operators (personnel) carrying portable detectors and who are otherwise working in the oil and gas industrial environment. The status processors of conventional safety systems show portable gas detectors on the map as individual moving icons. However, there is no way to represent a group of many closely situated icons if the persons carrying the detectors are working as a group in close proximity. When such persons work in close proximity, this causes the display processor to show the device icons on top one another especially if there are many devices in a particular zone. In this situation it becomes especially difficult to identify one particular device and/or to click on it to show further details. Since the moving devices are shown on a map which is zoomable, it adds to further complication and confusion because the group is not always shown in the same manner while zooming in and out of particular areas of the map image.

Figure 2:
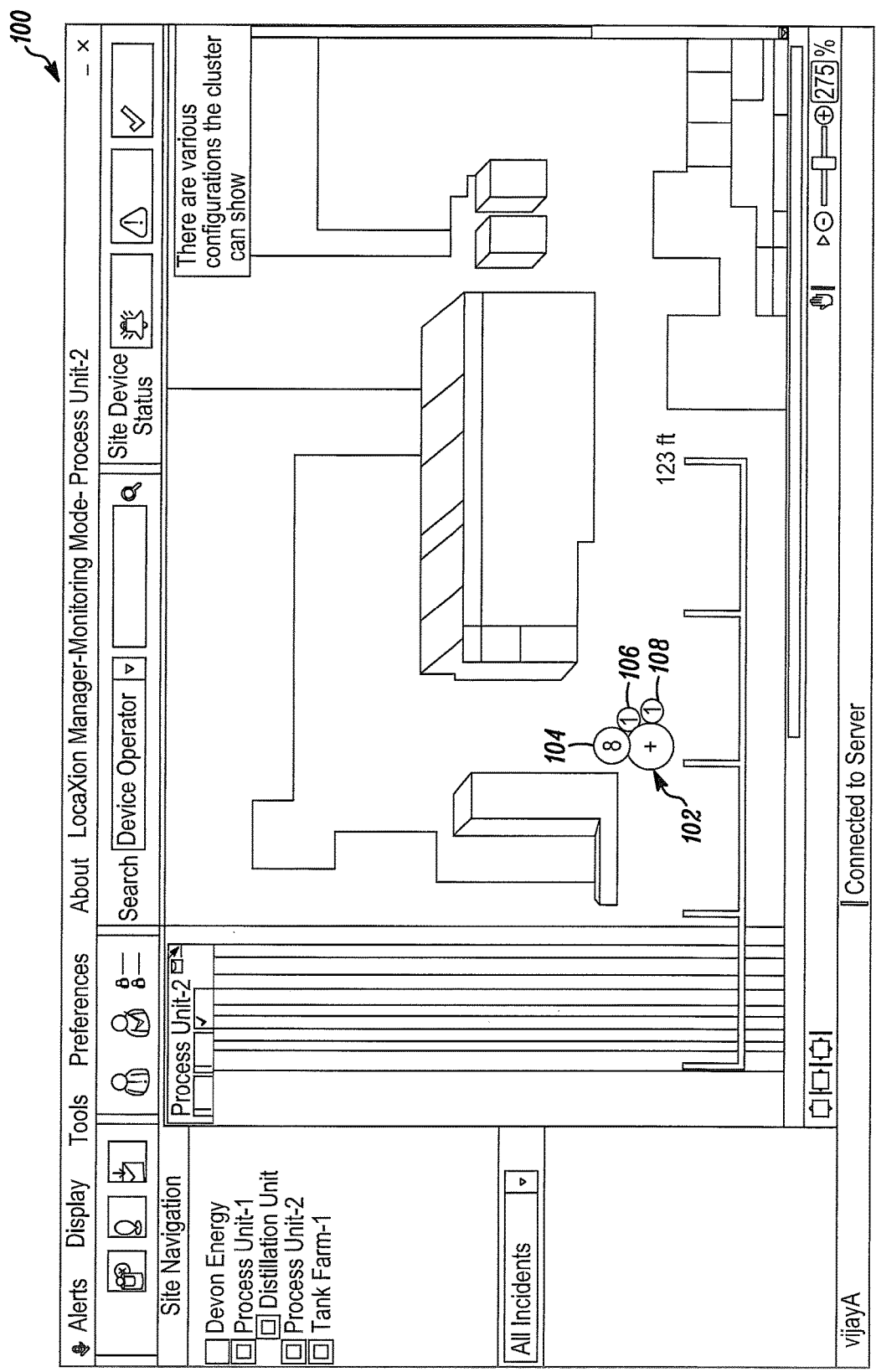
FIG. 2 illustrates a screen showing a map with a cluster icon.

The solution to this problem is to use a group or cluster icon whenever a group of detectors are within a predefined small area. For example, FIG. 2 depicts a screen 100 depicting a map of a monitored area. Included within the map is a group icon 102 that represents a group of portable gas detectors. FIG. 2 shows 10 portable gas detectors (8+1+1). Out of the ten, 8 devices are in alarm, one in fault and another in normal conditions.

As the scale of a given site image/map is known (and also by realizing from the on-screen scenario that it would be difficult to identify a single device at a particular viewable zoom level (before the images becomes pixelated)), it becomes clear that a parameter threshold can be used to control use of the group icon. The use of the threshold is based upon the concept that if five or more devices are close to each other in a particular area (e.g., a 10' by 10' block), then these devices may be shown as a cluster icon. The cluster icon is structured to include details including the number of devices and the status of each device displayed in conjunction with that cluster icon. For example, FIG. 2 depicts the number of alarmed devices represented by the icon shown within a circle 104 located directly adjacent the icon. In this case, the circle 104 (which can be a color indicator in some embodiments, for example shaded red for alarm) is located directly above the icon and includes a number equal to the number of alarmed gas detectors represented by that group icon. In this case, the group icon represents eight gas detectors and the number 8 is shown within the circle 104 directly above the group icon.

Similarly, the device with fault status may be represented within another circle 106 directly adjacent and to the upper right of the group icon. In this case, only one of the gas detectors is in fault status and the circle shows the number 1.

The normal status may also displayed within a third circle 108 shown directly adjacent and to the right of the group icon. In this case, only one of the ten gas detectors is in normal state and the circle contains the number 1.

Figure 3:
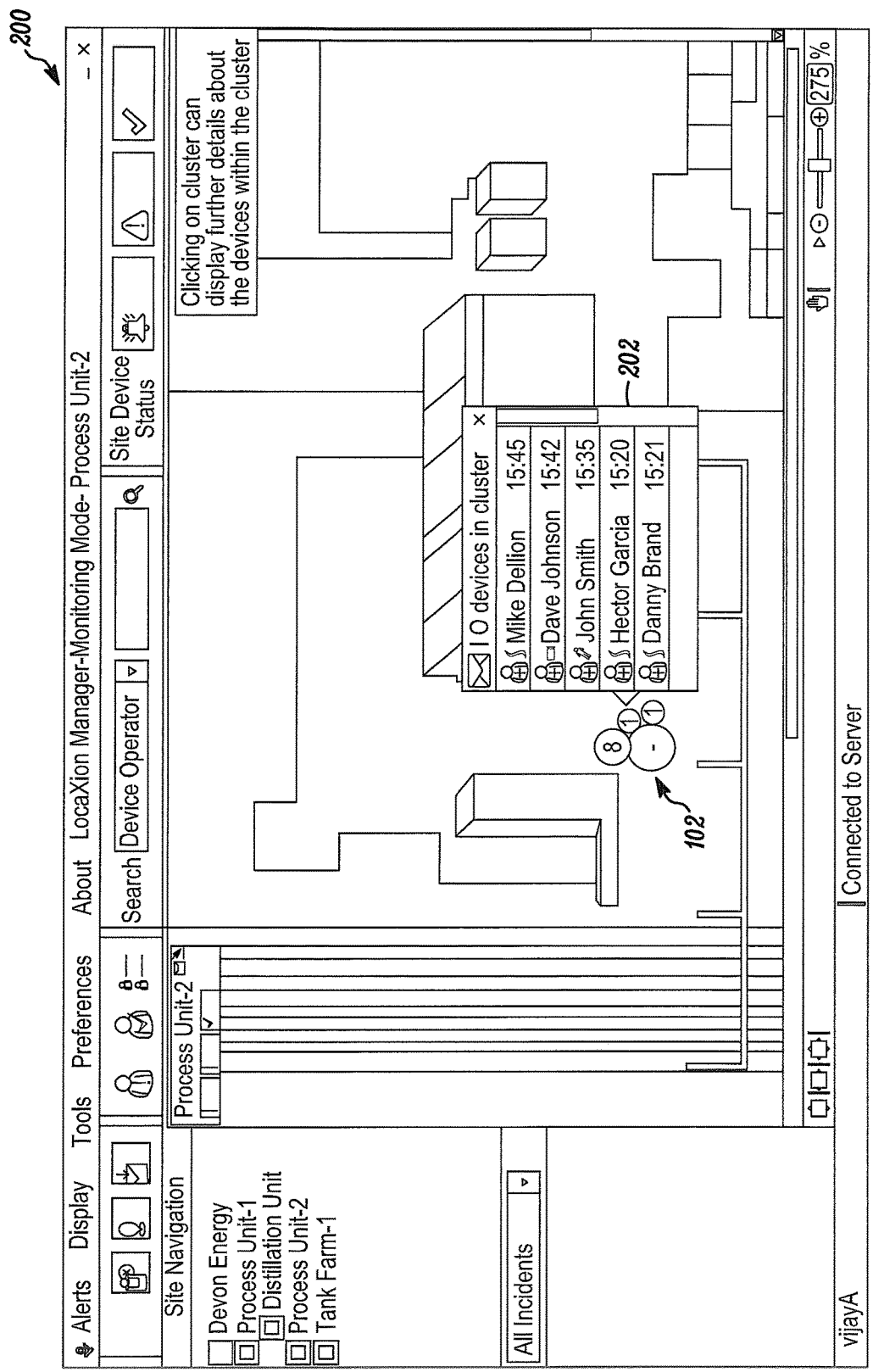
FIG. 3 illustrates a box showing the gas detectors represented by the cluster icon.

By clicking on the cluster icon, a user can display further details about the devices and their alarms, faults, etc. For example, FIG. 3 depicts a screen 200 where a user has clicked on the cluster icon. In response, a display processor shows a box 202 including partial list of the ten gas detectors and the status of each detector. The user can use the scroll bar on the right of the box to scroll through the remaining gas detectors represented by the cluster icon.

In general, the use of the cluster icon represents only part of the embodiment. Another significant part of the embodiment lies in identifying the correct parameter for controlling the use of the cluster icon based upon the realities of use and its practicality in being able to identify the detectors represented by the cluster icon.

For example, a 10 foot by 10 foot (10'×10') block or circle may be used as the parameter for grouping detectors and for replacing the grouped detectors with a single cluster icon. However, a selected parameter of a 10'×10' block may not be appropriate for all images and users. For example, the parameter may be expanded for use in other situations by other users (e.g., a 30'×30' block) or may be otherwise configurable based on the desired image clarity, the site size of the user and the location accuracy the user is seeking.

In general, the locations of the icons (portable detectors) shown on the map of dynamically adjusted based the moving position of each detector. Similarly, the details of the map are also dynamically changed based upon the zoom level. For example, Google maps reveals more data as one is zooming in and reveals less detail as a user zooms out. This is done to prevent the detail from obscuring the map's geographic reference points.

This combination of adjustments based upon both position and zoom level makes it very difficult to reliably read the maps displayed by the display processor. This is because the icons of the detectors at some point also begin to obscure the map's geographic reference points. Because of the balance between the number of detector icons and the map's detail, no standard size or standard for triggering the use of the group pixel can be established for all users. Hence, the use of group pixels based upon the level of map detail renders the concepts described herein different than the detector display methods of conventional security systems and also from conventional screen map visualizations (e.g., Google Maps, Zillow, etc.).

In order to use the detector display system of FIG. 1, a user first enters a configuration mode in order to set up the use of the group icon. In the configuration mode, a group icon is selected as a first step in order to set the scale for any given image. Once the scale is set, the user may be asked to provide location accuracy resolution that the user would want the application to support. Based on this resolution, the cluster parameter can be defined for a space from 10'×10' to 30'×30' or larger. As the detectors communicates with the server about their location, the display processor (or a related processor) begins to group detectors based upon their presence within some predefined area (e.g., 10'×10', 15'×15' etc.) of the map. If the status processor identifies any group of detects within that predefined area, the processor deletes those detector icons and replaces the deleted icons with a group icon centered over that predefined area. The use of the cluster icon is used irrespective of the zoom percentage imposed by a user on the map.

In general, the system incorporates the steps of a display of a gas detection system depicting a map of a predetermined geographic area and a plurality of portable gas detectors on the map via a respective gas detector icon, a programmed processor of the gas detection system identifying a number of gas detectors of the plurality of portable gas detectors within a predetermined portion of the area depicted on the display, the number exceeding a threshold value and a programmed processor of the gas detection system replacing the icons of the identified gas detectors within the portion with a group icon.

Alternatively, the system includes a gas detection system that uses a plurality of gas detectors to detect hazardous gases within a predetermined geographic area, a display of the gas detection system that depicts a map of the predetermined geographic area and the plurality of portable gas detectors on the map via a respective gas detector icon, a programmed processor of the gas detection system that identifies a number of gas detectors of the plurality of portable gas detectors within a predetermined portion of the area depicted on the display, the number exceeding a threshold value and a programmed processor of the gas detection system that replaces the icons of the identified gas detectors within the portion with a group icon.

Alternatively, the system includes a gas detection system that protects a predetermined geographic area, plurality of portable gas detectors of the gas detection system distributed throughout the area that detect hazardous gases, a display of the gas detection system that depicts a map of the area with the plurality of portable gas detectors displayed on the map via a respective gas detector icon, a programmed processor of the gas detection system that displays a status of each of the plurality of gas detectors on the map via a color indicator, a programmed processor of the gas detection system that identifies a number of gas detectors of the plurality of portable gas detectors within a predetermined portion of the area depicted on the display, the number exceeding a threshold value and a programmed processor of the gas detection system that replaces the icons of the identified gas detectors within the portion with a group icon.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

What is claimed is:

1. A method for indicating status of a plurality portable gas detectors, the method comprising:
   receiving sensed gas data, device information, and a geographic location from each of the plurality of portable gas detectors;
   depicting on a display i) a map of a predetermined geographic area and ii) a plurality of gas detector icons on the map, wherein the plurality of gas detector icons correspond to a geographic location for each of the plurality of portable gas detectors which are within the predetermined geographic area;
   identifying a number of gas detectors of the plurality of portable gas detectors which are within a predetermined portion of the area depicted on the display; and
   based on the number of gas detectors exceeding a threshold value within the predetermined portion of the area, replacing, on the display, the icons of the number of gas detectors identified within the predetermined portion of the area with a group icon and an alarm status icon directly adjacent the group icon,
   wherein the group icon indicates a numerical value for the number of gas detectors identified, and
   wherein the alarm status icon indicates a numerical value for the number of gas detectors identified which are in alarm.

2. The method as in claim 1, wherein the predetermined portion of the area has dimensions of less than X by Y feet or meters, wherein X by Y feet or meters comprises 10'×10'.

3. The method as in claim 2, wherein the step of replacing is performed irrespective of a zoom percentage of the map on the display.

4. The method as in claim 1, wherein the threshold value is five or more.

5. The method as in claim 1, further comprising:
   displaying a normal status icon directly adjacent the group icon, wherein the normal status icon indicates a numerical value for the number of gas detectors identified which are in a normal state.

6. The method as in claim 1, further comprising:
   comparing the received gas data from each of the plurality of portable gas detectors with a second threshold value for the gas data; and
   determining the gas data for at least one of the plurality of portable gas detectors exceeds the second threshold value.

7. The method as in claim 6, further comprising:
displaying the alarm status icon above the group icon.

8. The method as in claim 1, further comprising:
comparing the received device information from each of the plurality of portable gas detectors with a second threshold value;
determining a fault condition exists for at least one of the number of gas detectors identified.

9. The method as in claim 8, further comprising:
displaying a fault status icon directly adjacent the group icon, wherein the fault status icon indicates a numeral value for the number of gas detectors identified which have the fault condition.

10. The method of claim 1, wherein the alarm status icon is red in color.

11. The method of claim 1, wherein the alarm status icon is red in color.

12. An apparatus comprising:
a plurality of gas detectors; and
a control panel,
wherein each of the plurality of gas detectors is configured to communicate sensed gas data, device information, and a geographic location to the control panel,
wherein the control panel comprises a display of a user interface and one or more processors, wherein the display is configured to display i) a map of a predetermined geographic area and ii) a plurality of gas detector icons on the map, wherein the plurality of gas detector icons correspond to a geographic location for each of the plurality of gas detectors which are within the predetermined geographic area, wherein the one or more processors are configured to:
receive the sensed gas data, the device information, and the geographic location from each of the plurality of gas detectors,
identify a number of gas detectors of the plurality of portable gas detectors which are within a predetermined portion of the area depicted on the display, the number exceeding a threshold value; and
based on the number of gas detectors that exceeds the threshold value with the predetermined portion of the geographic area, replace, on the display, the gas detector icons of the number of gas detectors identified within the predetermined portion of the area with a group icon and an alarm status icon directly adjacent the group icon,
wherein the group icon indicates a numerical value for the number of gas detectors identified, and
wherein the alarm status icon indicates a numerical value for the number of s detectors identified which are in alarm.

13. The apparatus as in claim 12, wherein the predetermined portion of the area has dimensions of less than X by Y feet or meters, wherein X by Y feet or meters comprises 10'×10'.

14. The apparatus as in claim 13, wherein the display is further configured to replace the icons of the number of gas detectors identified within the predetermined portion of the area with a group icon irrespective of a zoom percentage of the map on the display.

15. The apparatus as in claim 12, wherein the threshold value is five or more.

16. The apparatus as in claim 12, wherein the display is further configured to display a normal status icon directly adjacent the group icon, wherein the normal status icon indicates a numerical value for the number of gas detectors identified which are in a normal state.

17. The apparatus as in claim 12, wherein the display is further configured to:
compare the sensed gas data received from each of the plurality of gas detectors with a second threshold value; and
determine the gas data for at least one of the plurality of detectors exceeds the second threshold value.

18. The apparatus as in claim 17, wherein the display is further configured to display the alarm status icon above the group icon.

19. The apparatus as in claim 12, wherein the display is further configured to:
compare the device information received from each of the gas detectors with a second threshold value; and
determine a fault condition exists for at least one of the number of gas detectors identified.

20. The apparatus as in claim 19, wherein the display is further configured to display a fault status icon directly adjacent the group icon, wherein the fault status icon indicates a numeral value for the number of gas detectors identified which have the fault condition.

* * * * *